United States Patent [19]

Sullivan et al.

[11] Patent Number: 5,584,687
[45] Date of Patent: Dec. 17, 1996

[54] PERFORMANCE ENHANCING DENTAL APPLIANCE

[75] Inventors: Maureen P. Sullivan, St. Paul, Minn.; Henry D. Cross, III, Murrell's Inlet, S.C.

[73] Assignee: E-Z Gard Industries, Inc., Minneapolis, Minn.

[21] Appl. No.: 375,921

[22] Filed: Jan. 19, 1995

Related U.S. Application Data

[63] Continuation of Ser. No. 104,489, Aug. 9, 1993, abandoned.

[51] Int. Cl.$^6$ ............................................. A61C 3/00
[52] U.S. Cl. ................................................. 433/6; 128/861
[58] Field of Search ................................ 433/6; 128/858, 128/859, 860, 861, 862

[56] References Cited

U.S. PATENT DOCUMENTS

| | | |
|---|---|---|
| 2,659,366 | 11/1953 | Savarese ................................. 128/861 |
| 3,126,002 | 3/1964 | Owens ................................... 128/861 |
| 4,519,386 | 5/1985 | Sullivan . | 
| 5,299,936 | 4/1994 | Ueno ................................. 128/861 X |
| 5,323,787 | 6/1994 | Pratt ................................. 128/861 X |
| 5,339,832 | 8/1994 | Kittlesen et al. ................... 128/861 X |

FOREIGN PATENT DOCUMENTS 1147583  6/1983  Canada ..................................... 433/6

*Primary Examiner*—Nicholas D. Lucchesi
*Attorney, Agent, or Firm*—Palmatier, Sjoquist, Helget & Voigt, P.A.

[57] ABSTRACT

A performance enhancing and force absorbing dental appliance for the mouth of an athlete is comprised of an occlusal posterior pad for each side of the posterior teeth engageable with the occlusal surfaces to space apart the teeth, to absorb shock and clenching stress. An arch is provided connecting the posterior pads together within the mouth and out of the way of the tongue to maintain the position of the occlusal posterior pads within the mouth during use and to prevent loss of the pads such as by swallowing.

23 Claims, 2 Drawing Sheets

PERFORMANCE ENHANCING DENTAL APPLIANCE

This application is a continuation of patent application Ser. No. 08/104,489 filed on Aug. 9, 1993, now abandoned, which is co-owned and shares common inventorship.

BACKGROUND OF THE INVENTION

This invention relates generally to a performance enhancing and force absorbing dental appliance for use by athletes, and more particularly to such an appliance that spaces apart the teeth to absorb shock and clenching stress, to space apart the anterior teeth of the lower and upper jaws to facilitate breathing and speech, to lessen condyle pressure, force and impact upon the cartilage and temporomandibular joints, the arteries and the nerves, and to further increase body muscular strength and endurance.

Almost all athletes, such as body builders, weight lifters, baseball batters, golfers, football players, hockey players and bowlers, clench their teeth during exertion which results in hundreds of pounds of compressed force exerted from the lower jaw onto the upper jaw. This clenching force is unevenly transmitted through the jaw structure into the connective tissues and muscles of the lower jaw and further into the neck and back. This can result in headaches, muscle spasms, damage to teeth, injury to the temporomandibular joint, and pain in the jaw. Furthermore, clenching the teeth makes breathing more difficult during physical exercise and endurance when breathing is most important.

There is a need for a performance enhancing and force absorbing dental appliance for the mouth of an athlete which will absorb shock and clenching stress otherwise transferred from the connective tissues, the muscles and lower jaw to the upper jaw, neck and back, will space apart the anterior teeth of the lower jaw from the anterior teeth of the upper jaw to facilitate breathing and speech, and will lessen condyle pressure, force and impact upon the cartilage, and temporomandibular joints, arteries and the nerves.

SUMMARY OF THE INVENTION

A performance enhancing and force absorbing dental appliance for the mouth of an athlete is comprised of an occlusal posterior pad for each side of the posterior teeth engageable with the occlusal surfaces to space apart the teeth, to absorb shock and clenching stress. An arch is provided connecting the posterior pads together within the mouth and out of the way of the tongue to maintain the position of the occlusal posterior pads within the mouth during use and to prevent loss of the pads such as by swallowing.

A principal object and advantage of the present invention is that the appliance protects the teeth, jaws, gums, connective tissues, back, head and muscles from teeth clenching forces typically exerted during athletic activity.

Another object and advantage of the present invention is that it facilitates breathing and speech during strenuous physical activity such as in power lifting or body building.

Another object and advantage of the present invention is that the appliance places the lower jaw in the power position moving the condyle downwardly and forwardly away from the nerves and arteries within the fossae or socket to increase body muscular strength, greater endurance and improved performance by the appliance user.

Other objects and advantages will become obvious with the reading of the following specification and appended claims with a review of the figures.

DETAILED SPECIFICATION

Figure 1:
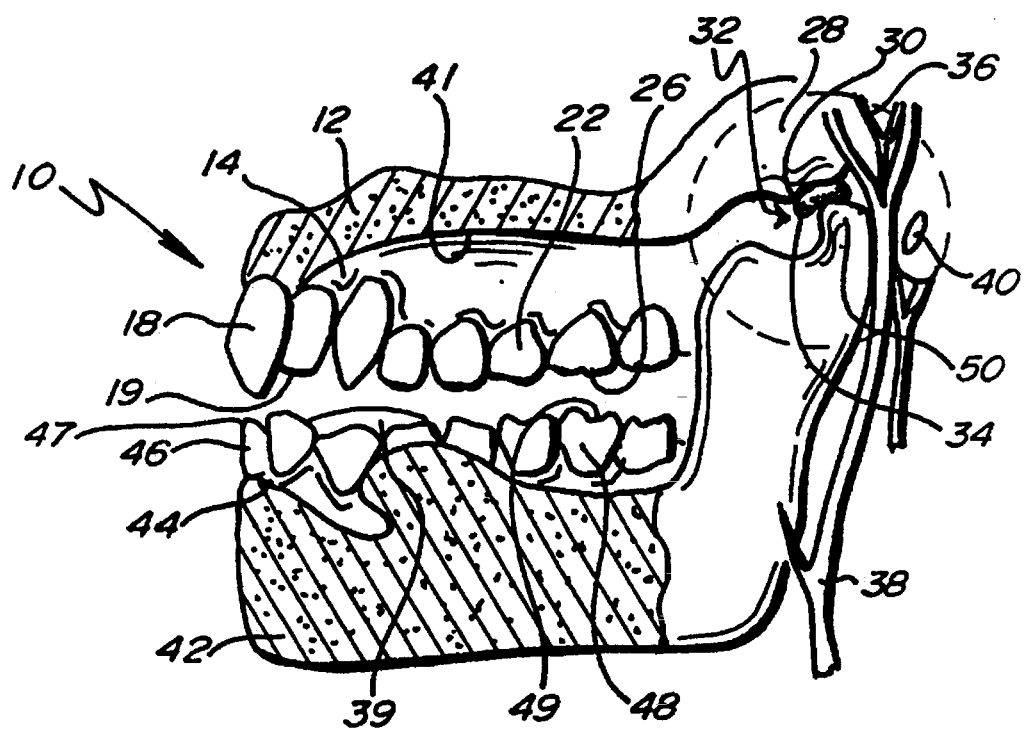
FIG. 1 is a maxillary mandibular buccal or partial side elevational view of the jaws and temporomandibular joint of the user of the dental appliance of the present invention.
Figure 1A:
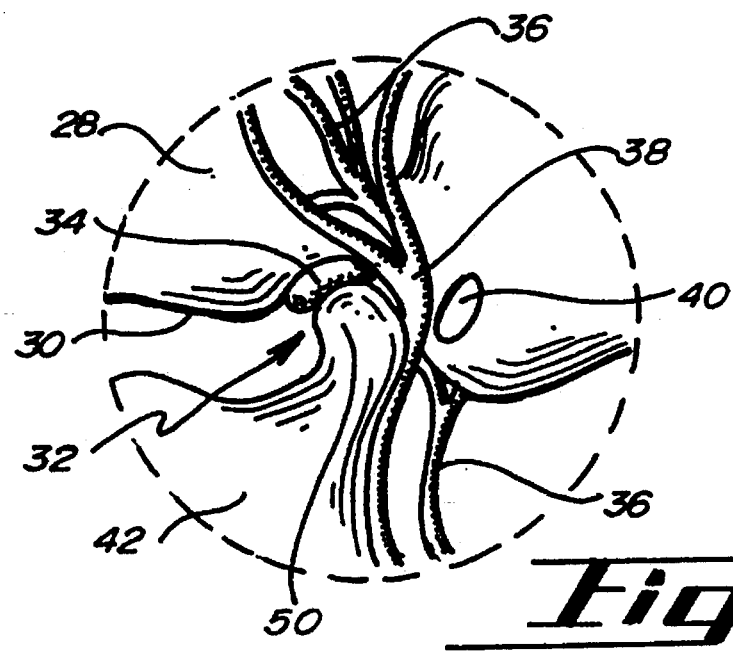
FIG. 1A is an enlarged view of the temporomandibular joint portion of FIG. 1.
Figure 2:
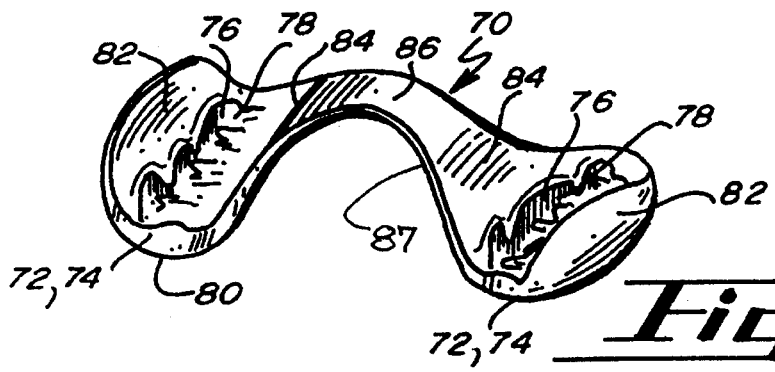
FIG. 2 is a perspective view of the performance enhancing and force absorbing dental appliance.
Figure 3:
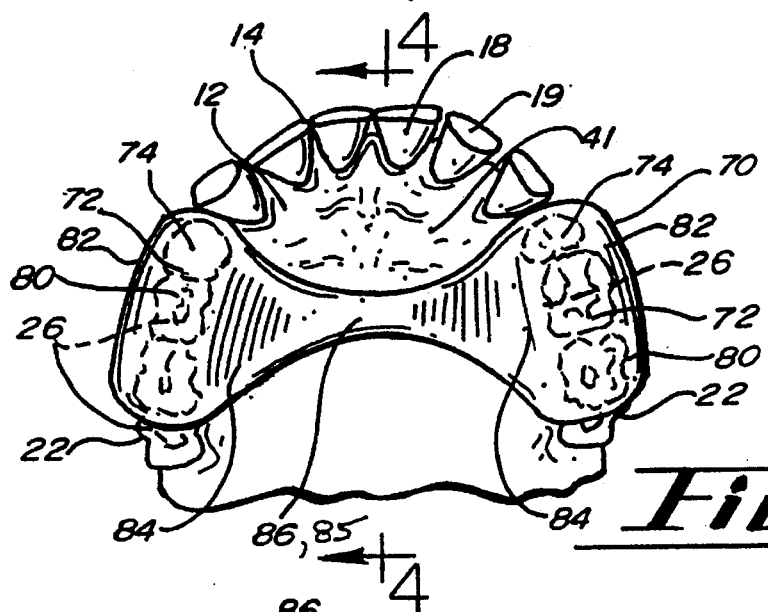
FIG. 3 is a bottom plan view of the upper jaw structure and teeth with the dental appliance in place.
Figure 4:
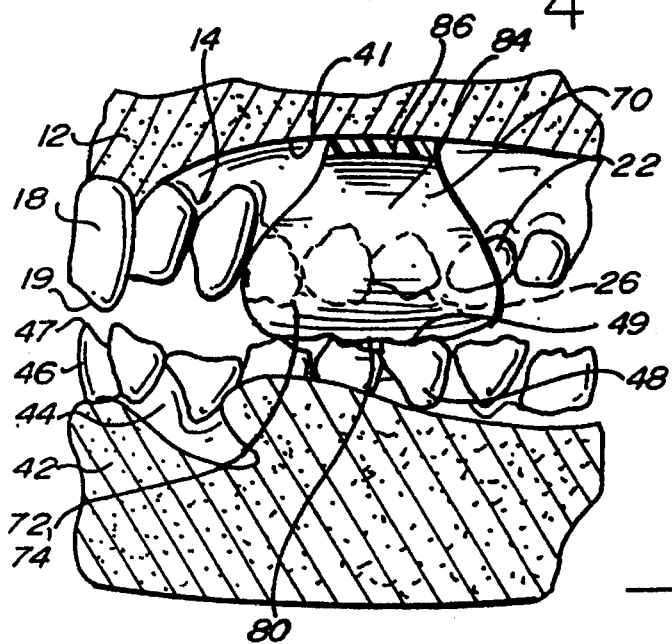
FIG. 4 is a cross-sectional view taken along lines 4—4 of FIG. 3.

To understand the structural features and benefits of the dental appliance 70 of the present invention, some anatomy will first be described. Referring to FIGS. 1 and 1A, the user or athlete has a mouth 10 generally comprised of a rigid upper jaw 12 and a moveable lower jaw 42 which are movably connected at the temporomandibular joint (TMJ) 32 and 50.

More specifically, the rigid upper jaw 12 has gum tissue 14 within mouth 10. Gum tissue 14, as well as the bone thereunder, supports anterior teeth (incisors and canines) 18 which have incisal or biting surfaces 19. The gum tissues 14 and the bone thereunder also support posterior teeth (molars and bicuspids) 22 which have cusps or biting surfaces 26.

Referring to one side of the human head, the temporal bone 28 is located upwardly and rearwardly of the upper jaw 12 and is in the range of $1/16$ to $1/32$ inch thick. The articular eminence 30 forms the beginning of the fossa 32 or the socket of the temporomandibular joint 32 and 50. Rearwardly and posteriorly to the articular eminence 30 is located cartilage 34. Through the temporomandibular joint 32 and 50 pass the auriculo-temporalis nerve 36 and the supra-temporo artery 38. Posteriorly to this structure is located the inner ear 40. Within the mouth is located tongue 39 and the roof or hard palate 31 which terminates rearwardly into the soft palate.

The movable jaw or mandible 42 supports a bone covered by gum tissue 44 which further supports anterior teeth (incisors and canines) 46 with incisal or biting surfaces 47 and posterior teeth (molars and bicuspids) 48 with occlusal biting surfaces 49. The condyle 50 of the lower jaw 42 forms the ball of the temporomandibular joint 32 and 50. The anatomical structure is the same for both sides of the head.

Repeated impacts, collisions, blows, stress or forces exerted on the movable lower jaw 42 result in excessive wearing forces upon the condyle 50 and the cartilage or disc 34—typically resulting in deterioration or slippage of the cartilage 34. Thereafter, the lower jaw 42 may be subject to irregular movement, loss of comfortable range of movement and clicking of the joint 32 and 50.

The auriculo-temporalis nerve 36 relates to both sensory and motor activity of the body. Any impingement or pinching of this nerve 36 can result in health problems as previously mentioned. The supra-temporal artery 38 is important in that it provides blood circulation to the head.

Impingement, pinching, rupture or blockage of this artery 38 will result in possible loss of consciousness and reduced physical ability and endurance due to the restriction of blood flow to the brain. Thus, it is extremely important to assure that the condyle 50 does not impinge upon the auriculo-temporalis nerve 36 or the supra-temporal artery 38.

It is also important to note that the temporal bone 28 is not too thick. Medical science has known that a sharp shock, stress, or concussive force applied to the lower jaw 42 possibly could result in the condyle 50 protruding through the temporal bone 28, thereby causing death. This incident rarely, but sometimes, occurs with respect to boxing athletes.

Referring to FIGS. 2 through 5, the power enhancing and shock absorbing dental appliance 70 may generally be seen. The appliance 70 is suitably integrally made of thermoplastic materials such as copolymers of ethylene and vinyl acetate. It has been found that ethylene vinyl acetate (EVA) is a commercially available compound and approved for oral use by the Food and Drug Administration.

The appliance 70 has posterior occlusal pads 72 each including a base 74 having a fitted top surface 76 with teeth indentations 78 for receiving the posterior teeth 22 of the upper jaw 12 as further explained below. The base 74 has a bottom surface 80 also somewhat conformable to the lower jaw posterior teeth 48. Extending upwardly from base 74 is the labial wall 82 and lingual wall 84. Extending directly across to and connecting the respective lingual walls 84 of both pads 72 is a connecting portion or continuous vertical arch 86 which is shaped as to lie along the palate 41 of the mouth and out of the way of the tongue 39. Preferably, the arch 86 is tapered along its central portion 85, thus reducing the weight of the appliance and minimizing contact with the palate and with the tongue.

Extending beneath the arch 86 and defined by the arch 86 and the lingual walls 84 of the pads 72 is a tunnel 87. The tunnel 87 is open anteriorly and posteriorly to allow unobstructed movement of the tongue anteriorly and posteriorly.

Figure 5:
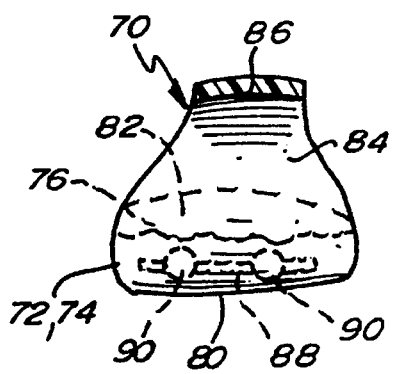
FIG. 5 is a cross-sectional view similar to the appliance in FIG. 4 showing another embodiment.

Optionally, the posterior occlusal pads 72 may have cushions 88 embedded therein appropriately with enlarged portions 90 (FIG. 5). The cushions 88 should suitably be made of a thermoplastic rubber such as that marketed under the trademark Kraton® which is marketed by GLS Plastics of 740B Industrial Drive, Gary, Ill. 60013. This thermoplastic rubber is unique in that it is injection-moldable, FDA approved and readily adheres with copolymers of ethylene and vinyl acetate. Furthermore, the thermoplastic rubber has a melting or softening point significantly higher than that of EVA which will facilitate fitting of the dental appliance 70 to the user or athlete's mouth 10. Furthermore, the thermoplastic rubber, unlike copolymers of ethylene and vinyl acetate, exhibits high resilience, low compression, shape maintenance and shock absorption, attenuation and dissipation. Virtually all rubbers exhibit these physical characteristics which may be utilized for the elastomeric cushion 88.

The enlarged portions 90 of embedded cushion 88 are arranged suitably to be in the bicuspid or molar regions of the teeth 22 and 49. The enlarged portions 90 may take the form of spheres, columns or knobs.

The cushion 88, and optionally the enlarged portions 90, together with the posterior occlusal pads 72 cause the mandible or lower jaw 42 to slide forwardly and slightly downwardly while fitting the dental appliance 70. Also, the condyles 50 are moved downwardly and away from the fossae or sockets 32 without the need for exotic devices and/or measurements, articulation, etc. Furthermore, the posterior cushions 88 and optional enlarged portions 90 assure proper fitting of the appliance 70 when the pads 72 are softened thereby prohibiting the user or athlete from biting too deeply into the soft EVA material of the occlusal pads 72 during fitting.

As is also to be appreciated, the occlusal pads 72 space apart the anterior teeth 18 and 46 while the arch 86 is clear of the tongue 39 and the tongue can move freely anteriorly and posteriorly in the tunnel 87 which will readily permit the wearer to easily breathe in power fashion as well as convey the ability to speak clearly.

In operation, the appliance 70 may be momentarily submersed suitably in boiling water. Thereafter, the appliance 70 is immediately placed onto the posterior teeth 22 of the upper jaw 12. Next, the lower jaw 42 is positioned forwardly or anteriorly in a range of one to four millimeters as the posterior teeth 48 of the lower movable jaw 42 are positioned on the bottom surface 80 of appliance 70. The wearer or user then applies suction between the upper jaw 12 and the appliance 70 while packing the appliance 70 with the hands along the cheeks adjacent the posterior teeth 22 of the upper jaw 12. The tongue 39 may force and conform the arch 86 to the palate 41 of the mouth 10.

By this action, the user of the appliance 70 will have correct jaw posture for athletic participation once fitting has been completed and the appliance 70 has cooled. The posterior teeth 48 of the lower jaw 42 will properly index upon the bottom surfaces 80 of the occlusal pads 72. Should the cushions 88 optionally be embedded within the pads 72, they will absorb, attenuate and dissipate shock and stress forces, such as created by clenching. Furthermore, the user will experience increased endurance, performance and muscular freedom due to the power positioning and posture of the TMJ joints 32 and 50.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

We claim:

1. A performance enhancing and force absorbing dental appliance adapted to lie within the mouth of an athlete having an upper jaw with anterior teeth, posterior teeth with occlusal surfaces, a palate and fossae with cartilage forming sockets, a tongue, and a moveable jaw with anterior teeth, posterior teeth with occlusal surfaces and condyles movably fitted with connective tissues and muscles within the sockets forming the temporomandibular joints through which the auriculo-temporalis nerves and supra-temporal arteries pass, the appliance comprising:

(a) a pair of occlusal posterior pads for the posterior teeth on each side of the mouth engageable with the occlusal surfaces to space apart the teeth, to absorb shock and clenching stress otherwise transferred from the connective tissues, the muscles and the lower jaw to the upper jaw, neck and back, to space apart the anterior teeth of the lower jaw from the anterior teeth of the upper jaw to facilitate breathing and speech, and to lessen condyles pressure, force and impact upon the cartilage, and temporomandibular joints, the arteries and the nerves;

(b) a continuous arch open anteriorly and posteriorly, extending directly across to and connecting the posterior pads together within the mouth which is shaped as to lie along the palate and out of the way of the tongue to maintain the positions of the occlusal posterior pads within the mouth and to prevent loss of the pads such as by swallowing, said arch having a width narrower than the width of the pads and (c) a tunnel beneath the arch and defined by the arch and the occlusal posterior pads, the tunnel being completely open anteriorly and posteriorly thereby allowing unobstructed movement of the tongue anteriorly and posteriorly.

2. The appliance of claim 1, wherein the occlusal posterior pads each have a top surface, a labial wall and a lingual wall conforming to posterior teeth of the upper jaw.

3. The appliance of claim 2, wherein the arch extends from the lingual walls of the occlusal posterior pads.

4. The appliance of claim 1, wherein the arch is tapered transversely along its central portion.

5. The appliance of claim 1, wherein the appliance is made of a low temperature, moldable, thermal plastic.

6. The appliance of claim 5, wherein the thermal plastic is ethylene vinyl acetate.

7. The appliance of claim 5, wherein the pads each have a posterior cushion made of a shock absorbing, nonsoftening, resilient, low compression elastomer embedded therein.

8. The appliance of claim 7, wherein the cushions are made of thermoplastic rubber.

9. The appliance of claim 7, wherein the cushions each have enlarged portions.

10. A performance enhancing and force absorbing thermoplastic dental appliance adapted to lie within the mouth of an athlete having an upper jaw with anterior teeth, posterior teeth with occlusal surfaces, a palate and fossae with cartilage forming sockets, a tongue, and a moveable jaw with anterior teeth, posterior teeth with occlusal surfaces and condyles movably fitted with connective tissues and muscles within the sockets forming the temporomandibular joints through which the auriculo-temporalis nerves and supra-temporal arteries pass, the appliance comprising:

(a) a pair of occlusal posterior pads for the posterior teeth on each side of the mouth engageable with the occlusal surfaces to space apart the teeth, to absorb shock and clenching stress otherwise transferred from the connective tissues, the muscles and the lower jaw to the upper jaw, neck and back, to space apart the anterior teeth of the lower jaw from the anterior teeth of the upper jaw to facilitate breathing and speech, and to lessen condyles pressure, force and impact upon the cartilage, and temporomandibular joints, the arteries and the nerves;

(b) a continuous vertical arch open anteriorly and posteriorly, adapted to lie along the palate out of the way of the tongue extending directly across to and connecting the posterior pads together within the mouth and out of the way of the tongue to maintain the positions of the occlusal posterior pads within the mouth and to prevent loss of the pads such as by swallowing, said arch having a width narrower than the width of the pads and (c) a tunnel beneath the arch and defined by the arch and the occlusal posterior pads, the tunnel being completely open anteriorly and posteriorly thereby allowing unobstructed movement of the tongue anteriorly and posteriorly.

11. The appliance of claim 10, wherein the occlusal posterior pads each have a top surface, a labial wall and a lingual wall conforming to posterior teeth of the upper jaw.

12. The appliance of claim 11, wherein the arch extends from the lingual walls of the occlusal posterior pads.

13. The appliance of claim 10, wherein the arch is tapered along its central portion.

14. The appliance of claim 10, wherein the thermal plastic is ethylene vinyl acetate.

15. The appliance of claim 10, wherein the pads each have a posterior cushion made of a shock absorbing, nonsoftening, resilient, low compression elastomer embedded in the pad.

16. The appliance of claim 15, wherein the cushions are made of thermoplastic rubber.

17. The appliance of claim 15, wherein the cushions each have enlarged portions.

18. A performance enhancing and force absorbing dental integral appliance adapted to lie within the mouth of an athlete having an upper jaw with anterior teeth, posterior teeth with occlusal surfaces, a palate and fossae with cartilage forming sockets, a tongue, and a moveable jaw with anterior teeth, posterior teeth with occlusal surfaces and condyles movably fitted with connective tissues and muscles within the sockets forming the temporomandibular joints through which the auriculo-temporalis nerves and supra-temporal arteries pass, the appliance comprising:

(a) a pair of occlusal posterior pads with a base having a top surface, a labial wall and a lingual wall conforming to the posterior teeth of the upper jaw on each side of the mouth engageable with the occlusal surfaces to space apart the teeth, to absorb shock and clenching stress otherwise transferred from the connective tissues, the muscles and the lower jaw to the upper jaw, neck and back, to space apart the anterior teeth of the lower jaw from the anterior teeth of the upper jaw to facilitate breathing and speech, and to lessen condyles pressure, force and impact upon the cartilage, and temporomandibular joints, the arteries and the nerves;

(b) a continuous vertical arch open anteriorly and posteriorly, extending from the lingual walls of the occlusal posterior pads and tapered transversely along its central portion and adapted to lie along the palate out of the way of the tongue extending directly across to and connecting the posterior pads together within the mouth and out of the way of the tongue to maintain the positions of the occlusal posterior pads within the mouth and to prevent loss of the pads such as by swallowing; and (c) a tunnel beneath the arch and defined by the arch and the occlusal posterior pads, the tunnel being completely open anteriorly and posteriorly thereby allowing unobstructed movement of the tongue anteriorly and posteriorly.

19. The appliance of claim 18, wherein the appliance is made of a low temperature, moldable, thermal plastic.

20. The appliance of claim 19, wherein the thermal plastic is ethylene vinyl acetate.

21. The appliance of claim 19, wherein the pads each have a posterior cushion made of a shock absorbing, nonsoftening, resilient, low compression elastomer embedded therein.

22. The appliance of claim 21, wherein the cushions are made of thermoplastic rubber.

23. The appliance of claim 21, wherein the cushions each have enlarged portions.

* * * * *

UNITED STATES PATENT AND TRADEMARK OFFICE
CERTIFICATE OF CORRECTION

PATENT NO. : 5,584,687
DATED : December 17, 1996
INVENTOR(S) : Maureen P. Sullivan; Henry D. Cross, III It is certified that error appears in the above-indentified patent and that said Letters Patent is hereby corrected as shown below:

Column 4, line 63, please insert the word --vertical-- after the word "continuous".

Column 6, line 3, please insert the word --transversely-- after the word "tapered".

Signed and Sealed this

First Day of July, 1997

Attest:

BRUCE LEHMAN

Attesting Officer

Commissioner of Patents and Trademarks